United States Patent
Ekimoto et al.

(10) Patent No.: US 6,500,816 B1
(45) Date of Patent: Dec. 31, 2002

(54) REMEDIES FOR PHOTOCHEMOTHERAPY

(75) Inventors: Hisao Ekimoto, Tokyo (JP); Masao Onishi, Yono (JP); Chieko Seno, Tokyo (JP); Teruyuki Sakai, Tokyo (JP)

(73) Assignee: Nippon Kayaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/786,874

(22) PCT Filed: Sep. 16, 1999

(86) PCT No.: PCT/JP99/05038

§ 371 (c)(1),
(2), (4) Date: Mar. 12, 2001

(87) PCT Pub. No.: WO00/16806

PCT Pub. Date: Mar. 30, 2000

(30) Foreign Application Priority Data

Sep. 17, 1998 (JP) .............................................. 10-263249

(51) Int. Cl.$^7$ ...................... A61K 31/555; A61B 5/055; A61B 5/00; G03C 1/00
(52) U.S. Cl. .................... 514/185; 424/9.61; 424/9.362; 430/270.1
(58) Field of Search ................................. 514/204, 202, 514/396, 185; 428/64.8, 913, 64.4; 430/270.19

(56) References Cited

U.S. PATENT DOCUMENTS

| | | | | |
|---|---|---|---|---|
| 3,670,025 A | * | 6/1972 | Susi ........................... 260/576 |
| 4,425,161 A | * | 1/1984 | Shibahashi et al. ........... 106/21 |
| 4,651,739 A | | 3/1987 | Oseroff et al. ............... 128/395 |
| 5,108,873 A | * | 4/1992 | Fukui et al. ................. 430/270 |
| 5,605,732 A | * | 2/1997 | Mihara et al. .............. 428/64.8 |

FOREIGN PATENT DOCUMENTS

WO 97/13490 4/1997

OTHER PUBLICATIONS

Tetrahedron Letters, vol. 34, No. 40, pp. 6359–6362, 1993; Phadke, et al.; "Synthesis of New Long Red Absorbing Porphyrins: Reactions of Organolithiums on Octaethylporphyrinone".

SPIE vol. 1203 Photodynamic Therapy: Mechanisms II (1990)/281–286; C.K. Chang et al.; "Synthetic Approachesto Long–Wavelength Absorbing Photsensitizers: Porphyrinone and Derivatives".

Sh. Nauchn. Prikl. Fotogr., 1997, vol. 42, No. 5. pp. 54–71; Tolmachev, A.J., et al.; "Chemistry polymethyne dyes for the near–IR region".

Journal of Photochemistry and Photobiology B: Biology 38 (1997) 178–183; Sonja Fickweiler, et al.; "Indocyanine green: Intracellular uptake and phototherapeutic effects in vitro".

SPIE vol. 3191; Gunter Schnurpfeil, et al.; "Photooxidative stability of various tetraazaporphyrin derivatives in solution and correlation with semiempirical MO–calculations", 1997.

J. Photochem. Photobiol. B: Biol., 23 (1994) 35–42; M. Shopova, et al.; "Hydrophobic Zn(II)–naphthalocyamines as photodynamic therapy agents for Lewis lung carcinoma".

Izv. Acad. Nauk., Ser. Khim., 1994, No. 12, pp. 2071–2082; Woehrle, D. et al. "Metal chelates of porphyrin derivatives a sensitizers in photooxidation of sulphur compounds and in photodynamic therapy of cancer".

Copy of the International Search Report dated Dec. 21, 1999.

\* cited by examiner

Primary Examiner—Zohreh Fay
Assistant Examiner—Brian Kwon
(74) Attorney, Agent, or Firm—Nields & Lemack

(57) ABSTRACT

Effective treatment of tumors, especially carcinomas, can be achieved by administering to man a photochemotherapeutic agent containing as an active ingredient a compound showing maximum absorption in the wavelength region of 800 to 1,200 nm, and then applying light rays of a wavelength of 800 to 1,200 nm.

8 Claims, No Drawings

REMEDIES FOR PHOTOCHEMOTHERAPY

This application is a 371 of PCT/JP99/05038 Sep. 16, 1999.

TECHNICAL FIELD

The present invention relates to a photochemotherapeutic agent which is effective for the treatment of, for example, tumors, especially carcinomas.

BACKGROUND ART

Presently, photochemotherapy is in practice as one of the effective therapeutics for tumors such as carcinomas. Studies on photochemotherapy were begun relatively early, and its clinical application was practiced in as early as 1976. A lot of literatures and patents on this subject have been issued, an example of which is a review by Michael J. Manya et al (J. Clin. Oncology, 6, 380, 1988). According to these literatures and patents, the compounds which have hitherto been studied and clinically applied as photochemotherapeutic agents are mostly the porphyrin-based compounds, and in Japan at present, Nippon Lederle is marketing dihematoporphyrin under the trade name of Photofrin®.

The photochemotherapy using such porphyrin-based compoudns are explained below.

When a drug is administered to a cancer patient (in case no surgical treatment is involved, the type of cancer to which the said therapeutics can be applied is limited in principle to cancer at the region close to the body surface, such as skin cancer, etc.), the best part of the drug is metabolized in the normal cells in several days, whereas the drug taken up by the cancerous cells stays left in the cells. The amount of the drug left in the cancerous cells is several to several ten times that in the normal cells. When light with a wavelength of 600 to 700 nm is applied to the cancerous cells, only these cells holding the drug die out specifically while the normal cells remain unaffected. The reason why the drug stays left in the cancerous cells alone is yet to be elucidated, but it is considered that this phenomenon is due to the difference in blood flowing condition between the normal and cancerous cells, or the difference in activity of the immune system such as lymphoid cells, etc. Also, no definite explanation is available on the reason why the cancerous cells holding the drug are killed by the application of light, but this seems to be attributable to the transformation of ambient oxygen into singlet oxygen having stronger toxicity by the transfer of energy from the drug activated by light exposure.

However, photochemotherapy using the said porphyrin-based compounds has some problems. One of such problems is in the relation between the absorption wavelength of the compound itself and the wavelength of light used for the treatment. The wavelength of light used for the treatment is preferably not less than 600 nm as it is required that the light applied won't be scattered or absorbed by the matters in the living body, and that no influence be given to the hemoglobin of the erythrocytes, and so on. However, absorption of light by, for instance, Photofrin® mentioned above as a commercial product of dihematoporphyrin in the wavelength region of not less than 600 nm is only 2 to 3% of that at the maximum absorption wavelength, 363 nm, of this compound. There is therefore no alternative but to practice a photochemotherapy which is actually very bad in efficiency, and this produces the necessity of increasing dosage of the drug or exposure dose of light, resulting in an increase of side effects or a rise of equipment cost.

Another problem is phototoxicity of the porphyrin-based compounds in the skin, etc., and because of this, the drug-administered patient is obliged to lead a life avoiding exposure to light such as sunlight for about 6 to 8 weeks. Still another problem is the limited range of treatment since the penetration into the tissue of the light rays of a wavelength region of around 630 nm is only several mm. This has been an obstacle to the clinical application of the above compounds.

DISCLOSURE OF THE INVENTION

The present invention is intended to provide an utterly new type of photochemotherapeutic agent for solving the said prior art problems.

The present inventors found out a photochemotherapeutic agent having high tissue penetrability and strong absorbability from among the functional pigments, and attained the present invention on the basis of this finding. Thus, the present invention relates to the following items of disclosure (1) to (30).

(1) A photochemotherapeutic agent comprising as an active ingredient a compound showing maximum absorption at wavelengths from 800 to 1,200 nm.

(2) A photochemotherapeutic agent comprising as an active ingredient a diimonium type compound showing maximum absorption in the wavelength region of 800 to 1,200 nm.

(3) A photochemotherapeutic agent according to (2) above, wherein the diimonium type compound is a compound having a skeletal structure represented by the formula (12):

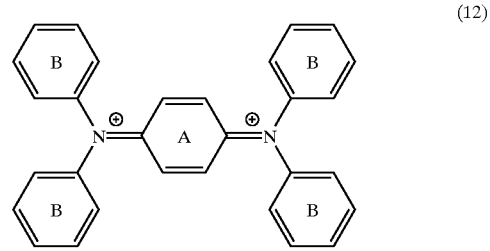

(4) A photochemotherapeutic agent according to (2) above, wherein the diimonium type compound is a compound represented by the following formula (3) or its pharmacologically acceptable salt:

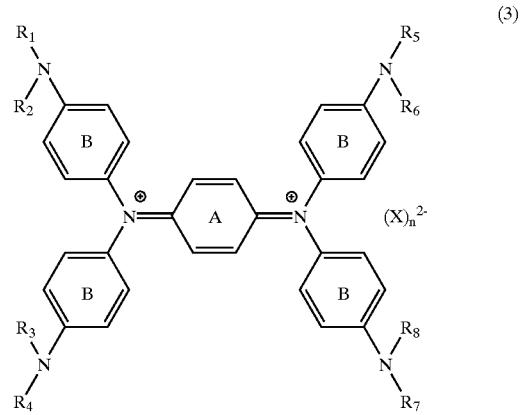

wherein $R_1$ to $R_8$ represent independently a C1–C12 substituent; X represents an anion: n is a number of 1 or 2; and ring A and four ring B's may have independently of each other 1 to 4 substituents.

(5) A photochemotherapeutic agent according to (4) above, wherein $R_1$ to $R_8$ are each a hydrophobic group.
(6) A photochemotherapeutic agent according to (4) above, wherein $R_1$ to $R_8$ are each a C1–C5 group, and ring A and four ring B's have no substituent.
(7) A photochemotherapeutic agent comprising as an active ingredient an aminium type compound showing maximum absorption in the wavelength region of 800 to 1,200 nm.
(8) A photochemotherapeutic agent according to (7) above, wherein the aminium type compound is a compound having a skeletal structure represented by the formula (13):

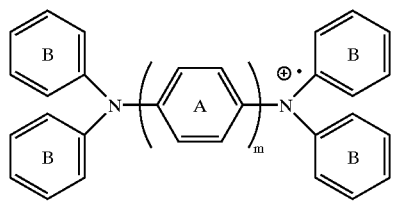

(13)

wherein m is a number of 1 or 2.
(9) A photochemotherapeutic agent according to (7) above, wherein the aminium type compound is a compound represented by the following formula (4) or its pharmacologically acceptable salt:

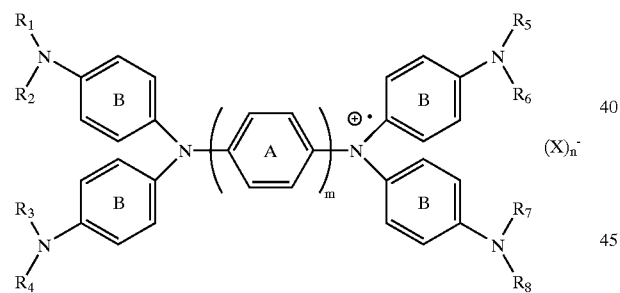

(4)

wherein $R_1$ to $R_8$ represent independently a C1–C12 substituent; X represents an anion; n is a number of 1 or 1/2; m is a number of 1 or 2; and 1 or 2 ring A's and four ring B's may have independently of each other 1 to 4 substituents.
(10) A photochemotherapeutic agent according to (9) above, wherein $R_1$ to $R_8$ are each a hydrophobic group.
(11) A photochemotherapeutic agent according to (9) above, wherein $R_1$ to $R_8$ are each a C1–C5 alkyl group, m is 1, and ring A and four ring B's have no substituent.
(12) A photochemotherapeutic agent according to (1) above, wherein the compound is a naphthalocyanine type compound or an anthracyanine type compound.
(13) A photochemotherapeutic agent according to (12) above, wherein the compound is a compound of the following formula (1) or (2) or its pharmacologically acceptable salt:

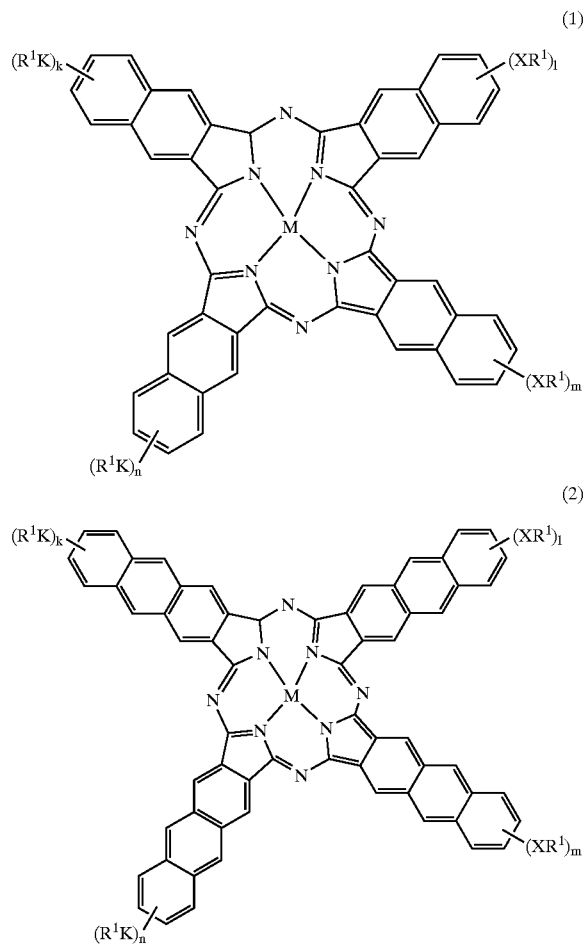

wherein X represents an oxygen atom, a sulfur atom, NH, $SO_2$, CO or a single bond; $R^1$ represents an optionally substituted aryl, aralkyl or alkyl group, an alkoxyl group, an alkylamino group or a hydroxyl group; k, l, m and n represent respectively an integer of 0 to 4, and when k+l+m+n is equal to 2 or greater, $R^1$ and X may be identical or different; and M represents a metal or an oxidized metal which may have coordinated therein one or more of the ligands such as a halogen atom, a hydroxyl group, an aryloxy group, an alkoxyl group, a trialkylsiloxy group, a triarylsiloxy group, a trialkoxysiloxy group, a triaryloxysiloxy group, a trityloxy group, an acyloxy group, etc.
(14) A photochemotherapeutic agent according to (1) above, wherein the compound is a complex compound represented by the following formula (5) or its pharmacologically acceptable salt:

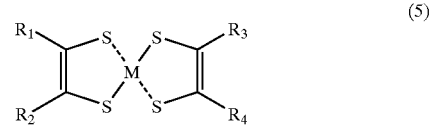

(5)

wherein $R_1$ to $R_4$ represent independently a hydrogen atom or an optionally substituted alkyl, aryl, alkylthio or arylthio group, or $R_1$ and $R_2$ and/or $R_3$ and $R_4$ may combine with each other to form a ring having a substituent; and M represents Ni, Pd, Co, VO, Cu or Pt.

(15) A photochemotherapeutic agent according to (1) above, wherein the compound is a bissquarilium type compound.

(16) A photochemotherapeutic agent according to (15) above, wherein the compound is a compound represented by the following formula (6) or its pharmacologically acceptable salt:

(6)

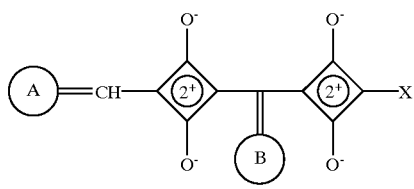

wherein ring A and ring B represent independently a heterocyclic ring containing a nitrogen atom; and X represents

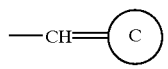

wherein ring C represents a heterocyclic ring containing a nitrogen atom,
or a benzene ring substituted with an alkylamino group.

(17) A photochemotherapeutic agent according to (1) above, wherein the compound is a metal-containing indoaniline type compound.

(18) A photochemotherapeutic agent according to (17) above, wherein the compound is a compound represented by the following formula (7) or its pharmacologically acceptable salt:

(7)

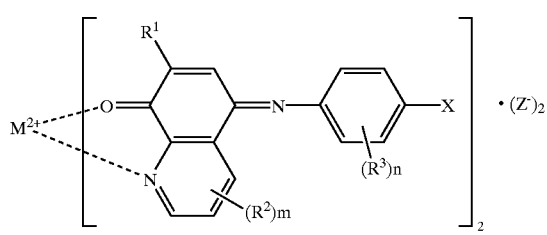

wherein M represents a chelatable metal ion; $R^1$ represents a hydrogen atom, an optionally substituted alkyl, aryl, arylalkyl, alkoxyl, alkylamino or alkylaminocarbonyl group, a halogen atom, a hydroxyl group, an amino group, an acylamino group, a sulfonylamino group, an aminocarbonyl group or a nitro group; $R^2$ and $R^3$ represent respectively a halogen atom or a monovalent organic group; X represents

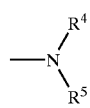

—$OR_6$ or a hydroxyl group; $Z^{31}$ represents an anion; $R_4$, $R_5$ and $R^6$ represent respectively an optionally substituted alkyl group; m and n are each an integer of 0 to 3, and when each of m and n is 2 or greater, $R^2$ and $R^3$ may be identical or different.

(19) A photochemotherapeutic agent according to (1) above, wherein the compound is a polymethine or other type compound (excluding the indocyanine type compounds) represented by any one of the following formulae (8) to (11), or its pharmacologically acceptable salt:

(8)

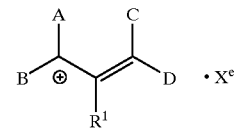

(9)

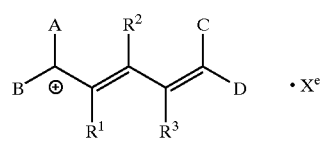

(10)

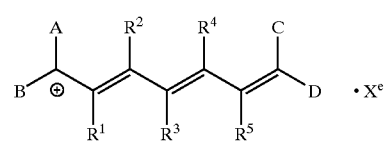

(11)

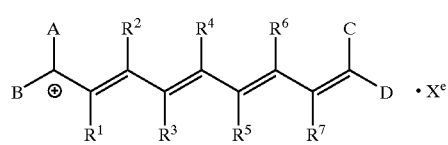

wherein $R^1$ to $R^7$ represent independently of each other a monovalent organic group residue such as a hydrogen atom, a halogen atom, an optionally substituted alkyl group, a hydroxyl group, an optionally substituted alkoxyl group, an amino group, etc., a saturated alicyclic group, an unsaturated alicyclic group, a saturated heterocyclic group, an aromatic-ring group, a heteroaromatic-ring group, a substituted aromatic-ring group or a substituted heretoaromatic-ring group, and at least one of the combinations $R^1$—$R^3$, $R^2$—$R^4$, $R^3$—$R^5$, $R^4$—$R^6$ and $R^5$—$R^7$ may form a ring which may be a 5-, 6- or 7-membered substituted or non-substituted saturated alicyclic ring, an unsaturated alicyclic ring, a saturated heterocyclic ring or aromatic ring, a heteroaromatic ring or a condensed ring thereof; A to D represent independently of each other a hydrogen atom, an optionally substituted aromatic ring, a heteroaromatic ring, a substituent represented by any one of the following formulae:

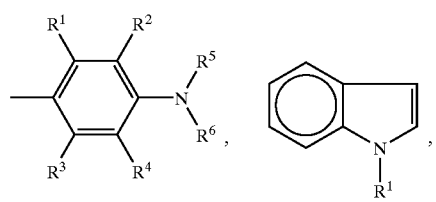

-continued

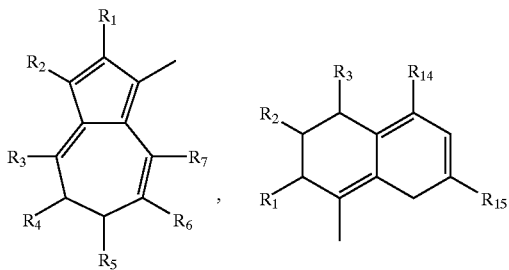

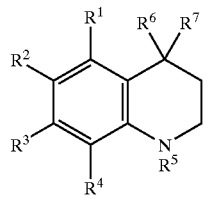

wherein a substitued or non-substituted condensed ring may be formed with at least one of the combinations $R^1$—$R^2$, $R^2$—$R^3$, $R^3$—$R^4$, $R^5$—$R^6$ and $R^6$—$R^7$, or a group having a hetero atom in the azulene skeleton, but 2 or more of A to D can not be a hydrogen atom at the same time; $R^1$ to $R^7$ are selected from the above-mentioned monovalent organic group residues, $Rl_{14}$ and $R_{15}$ are selected from the above-mentioned monovalent organic group residues and optionally substituted phenyl groups; A—B and C—D may form a ring to constitute a group represented by the following formula:

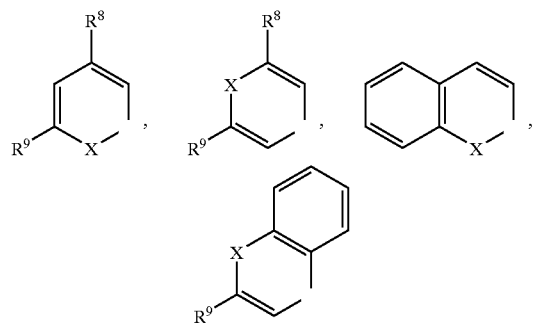

wherein $R^8$ and $R^9$ represent independently of each other an aromatic-ring group which may be substituted with a monovalent organic group residue such as a halogen atom, an alkyl group, a hydroxyl group, an alkoxyl group or an amino group, a styryl group or a heteroaromatic-ring group; and X represents a heteroatom such as an oxygen, a sulfur, a selenium or a tellurium atom, or a substituted nitrogen atom, or the following formulae:

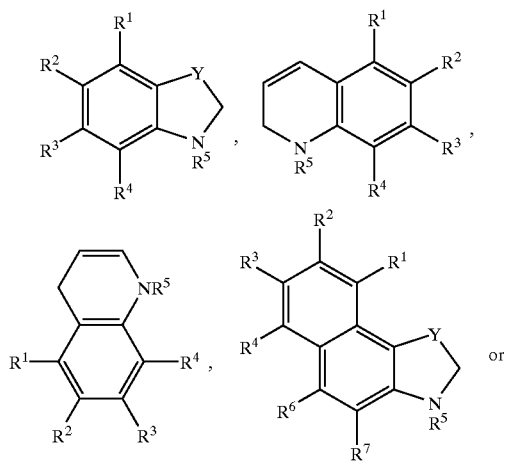

wherein Y represents a hetero-atom such as an oxygen, a sulfur, a selenium or a tellurium atom, a substituted or non-substituted methylene group, or a substituted nitrogen atom, but $R^1$ to $R^7$ are selected from the above-mentioned monovalent organic group residues; and X represents an anion.

(20) A photochemotherapeutic agent according to (1) above, wherein the compound is one having a radical in the molecule.

(21) A photochemotherapeutic agent according to any one of (1) to (20) above, which contains a pharmacologically acceptable carrier.

(22) A photochemotherapeutic agent according to (21) above, wherein the pharmacologically acceptable carrier is a solvent.

(23) A photochemotherapeutic agent according to (22) above, containing a compound according to any one of (1) to (20) above in a concentration of 0.1 to 100 mg/ml.

(24) A photochemotherapeutic agent according to (22) or (23) above, wherein the solvent is a physiological saline, a 5% glucose solution or a mannitol solution.

(25) A photochemotherapeutic agent according to (22) or (23) above, wherein the solvent is a water-soluble organic solvent such as glycerol, ethanol, dimethyl sulfoxide, polyethylene glycol or Cremophor.

(26) A photochemotherapeutic agent according to (22) or (23) above, wherein the solvent is a mixture of water and a water-soluble organic solvent.

(27) A photochemotherapeutic agent according to (25) or (26) above, wherein the water-soluble organic solvent is dimethyl sulfoxide or ethanol.

(28) A method for photochemotherapy of tumors which comprises administration of a photochemotherapeutic agent according to any one of (1) to (27) above, and then application light rays of a wavelength in the range of 800 to 1,200 nm.

(29) The method according to (28) above, wherein the administration is effected by applying the agent on the surface of a tumor or by directly injecting the agent into the tumor.

(30) The method according to (28) above, wherein the light rays are laser beams.

BEST MODE FOR CARRYING OUT THE INVENTION

The present invention is described in detail below.

The compounds showing maximum absorption in the wavelength region of 800 to 1,200 nm, which can be used as an active ingredient of the photochemotherapeutic agent of the present invention, are not restricted; it is possible to use, for example, naphthalocyanine type compounds, anthracyanine type compounds, diimonium type compounds especially those having a skeletal structure represented by the formula (12), aminium type compounds, especially those having a skeletal structure represented by the formula (13), bissquarilium type compounds, metal-containing indoaniline type compounds, polymethine type compounds, cyanine type compounds, azocyanine type compounds, and various kinds of complex compounds, but the compounds represented by any one of the formulae (1) to (11) or their pharmacologically acceptable salts are preferred. Especially, the diimonium type compounds having a skeletal structure represented by the formula (12), the aminium type compounds having a skeletal structure represented by the formula (13), and the compounds of the formulae (1) to (11) or their pharmacologically acceptable salts showing maximum absorption in the wavelength region of 930 to 1,100 nm are preferable.

In the formulae (12) and (13), when a nitrogen atom is attached to the 1-position, a substituted amino group may be attached to the 4-position of each of the four phenyl groups. The molecular extinction coefficient (ε) at the maximum absorption wavelength of the compounds used in the present invention is preferably $5 \times 10^3$ or above, more preferably $1 \times 10^4$ or above, especially $2 \times 10^4$ or above.

In the following, the compounds of the formulae (1) to (11) are described respectively in detail.

i) Compounds of Formulae (1) and (2)

The optionally substituted aryl groups include phenyl groups, naphthyl groups and heteroaromatic-ring compound residues which may have a substituent(s) such as alkyl group having preferably 1 to 15, more preferably 1 to 10 carbon atoms, and alkoxyl or alkylthio group having preferably 1 to 15, more preferably 1 to 10 carbon atoms. Actual examples of such groups include alkyl substituted phenyl or naphthyl groups such as phenyl, 4-methylphenyl, 2-methylphenyl, 2,4-dimethylphenyl, 4-ethylphenyl, 4-butylphenyl, 4-(tert-butyl)phenyl, 4-nonylphenyl and β-naphthyl group, alkoxy and/or alkylthio-substituted phenyl or naphthyl groups such as 4-methoxyphenyl, 4-butoxyphenyl, 4-octyloxyphenyl and 4-ethylthiophenyl group, and heteroaromatic-ring compound residues such as γ-pyridyl and 8-quinolyl group.

The optionally substituted aralkyl groups include benzyl groups and phenylethyl groups which may have a substituent(s) such as alkyl group having preferably 1 to 15, more preferably 1 to 3 carbon atoms, and alkoxyl group having preferably 1 to 5, more preferably 1 to 3 carbon atoms. Actual examples of such groups are benzyl, 2-phenylethyl, (4-methylphenyl)methyl and (4-ethoxyphenyl)methyl.

The optionally substituted alkyl groups include straight-chain alkyl groups such as methyl, ethyl, n-propyl, n-butyl, n-hexyl, n-nonyl and n-dodecyl group, and branched alkyl groups such as isopropyl, 2-methylpropyl, tert-butyl, tert-pentyl, neopentyl and 2-methylpentyl group. The carbon number of these alkyl groups is preferably 1 to 10, more preferably 1 to 6. The alkyl groups may have a substituent such as halogen atom, amino group, hydroxyl group, cyano group, carboxyl group, sulfonic group and a group of the formula

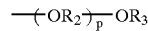

(wherein $R_2$ represents a C2–C3 alkylene group; $R_3$ represents a C1–C10, preferably C1–C6 alkyl group; and p is an integer of 0 to 10, preferably 0 to 6). The alkyl groups in the optionally substituted alkoxyl groups are the same as the above-mentioned optionally substituted alkyl groups. Also, the alkyl groups in the optionally substituted alkylamino groups are the same as the above-mentioned optionally substituted alkyl groups. These alkyl groups may be either mono-form or di-form, and in the latter case, the alkyl groups may be identical or different.

The letters k, l, m and n each represents an integer of 0 to 4, preferably 1 to 2. k+l+m+n is equal to 1 or a greater integer, preferably an integer of 4 to 8.

The metals represented by M include Cu, Ni, Mg, Pb, V, Si, Pd, Co, Nb, Al, Sn, Zn, Ca, In, Ga, Fe and Ge. Of these metals, Cu, Ni, Mg, Zn, V, Co and Si are preferred.

The halogen atoms which may be coordinated to M include F, Cl and Br. In the groups which may be coordinated to M, the aryl group is for instance phenyl, the alkoxyl group is for instance the one having 1 to 6 carbon atoms, the alkyl group is for instance the one having 1 to 6 carbon atoms, and the acyl group is for instance the one having 1 to 6 carbon atoms. In case a halogen or a group such as mentioned above is coordinated to M, the number of coordination is usually 1 to 2.

ii) Compounds of Formula (3)

The substituents, which can be existed on ring A or B, $R_1$ to $R_8$ and X are the same groups as those of compounds of formula (4) described below.

Also, the preferable substituents represented by $R_1$ to $R_8$ are the same as those of compounds of formula (4) described below.

When X is a monovalent anion, n is 2, and when it is a divalent anion, n is 1.

iii) Compounds of formula (4)

Ring A and each ring B may have 1 to 4 substituents or may not have any substituent. The substituents that can be attached to these rings include, for example, a halogen atom, a hydroxyl group, an alkoxyl group, a cyano group, a lower alkyl group. The halogen atom may be, for instance, fluorine atom, chlorine atom, bromine atom or iodine atom. As the alkoxyl group, a C1–C5 alkoxyl group such as methoxy group or ethoxy group is used. As the lower alkyl group, a C1–C5 alkyl group such as methyl group or ethyl group is used. Preferably, ring A has no substituent or is substituted with a halogen atom (especially chlorine or bromine atom), a methyl group or a cyano group. Each ring B is preferably possessed no substituent.

As the C1–C12 substituents represented by $R_1$ to $R_8$ in the above formulae, there can be cited, for instance, hydrophobic groups. Actual examples of such groups are alkyl, alkoxyalkyl, alkenyl, aralkyl and alkynyl. The alkyl groups include, for instance, methyl, ethyl, n-propyl, iso-propyl, n-butyl, sec-butyl, iso-butyl, t-butyl, n-amyl, t-amyl, h-hexyl, n-octyl and t-octyl group. Of these alkyl groups, those having 1 to 5 carbon atoms are preferred. Examples of the alkoxyalkyl groups are (C1–C4)alkoxy(C1–C4)alkyl groups such as methoxyethyl, ethoxyethyl and methoxypropyl group. The alkenyl groups include, for instance, vinyl, propenyl, butenyl, pentenyl, hexenyl, heptenyl and octenyl group. The alkenyl groups having 1 to 5 carbon atoms are preferred. The aralkyl groups include phenyl(C1–C4)alkyl groups such as benzyl, p-chlorobenzyl, p-methylbenzyl, 2-phenylethyl, 2-phenylpropyl and 3-phenylpropyl group, and naphthyl(C1–C4)alkyl groups such as α-naphthylmethyl and β-naphthylmethyl group. The alkynyl groups include C1–C5 alkynyl groups such as propagyl, butynyl, pentynyl and hexynyl. Of these groups, the alkyl groups having 1 to 5 carbon atoms are preferred.

X represents a monovalent or divalent anion. When it is a monovalent anion, n is 1, and when it is a divalent anion, n is 1/2. The monovalent anions rerpresented by X include organic acid monovalent anions and inorganic monovalent anions. Examples of the organic acid monovalent anions include organic carboxylate ions such as acetate ion, lactate ion, trifluoroacetate ion, propionate ion, benzoate ion, oxalate ion, succinate ion and stearate ion, organosulfonate ions such as methanesulfonate ion, toluenesulfonate ion, naphthalenemonosulfonate ion, chlorobenzenesulfonate ion, nitrobenzenesulfonate ion, dodecylbenzenesulfonate ion, benzenesulfonate ion, ethanesulfonate ion and trifluoromethanesulfonate ion, and organoborate ions such as tetraphenylborate ion and butyltriphenylborate ion. Halogenoalkylsulfonate ions or alkylarylsulfonate ions such as trifluoromethanesulfonate ion and toluenesulfonate ion are preferred.

The inorganic monovalent anions include halogen ions such as fluorine ion, chlorine ion, bromine ion and iodine ion, etc., thiocyanate ion, hexafluoroantimonate ion, perchlorate ion, periodate ion, nitrate ion, tetrafluoroborate ion, hexafluorophosphonate ion, molybdenate ion, tungstate ion, titanate ion, vanadate ion, phosphonate ion, and borate ion. Of these inorganic monovalent anions, perchlorate ion, iodate ion, tetrafluoroborate ion, hexafluorophosphonate ion and hexafluoroantimonate ion are preferred.

The divalent anions include the ions of naphthalenedisulfonic acid derivatives such as naphthalene-1,5-disulfonic acid, R-acid, G-acid, H-acid, benzoyl H-acid, p-chlorobenzoyl H-acid, p-toluenesulfonyl H-acid, chloro H-acid, chloroacetyl H-acid, metanil γ-acid, 6-sulfonaphthyl-γ-acid, C-acid, ε-acid, p-toluenesulfonyl R-acid, naphthalene-1,6-disulfonic acid, and 1-naphthol-4, 8-disulfonic acid, and the ions of divalent organic acids such as carbonyl J-acid, 4,4'-diaminostilbene-2,2'-disulfonic acid, di-J-acid, naphthalic acid, naphthalene-2,3-dicarboxylic acid, diphenic acid, stilbene-4,4'-dicarboxylic acid, 6-sulfo-2-oxy-3-naphthoic acid, anthraquinone-1,8-disulfonic acid, 1,6-diaminoanthraquinone-2,7-disulfonic acid, 2-(4-sulfophenyl)-6-aminobenzotriazole-5-sulfonic acid, 6-(3-methyl-5-pyrazolonyl)-naphthalene-1,3-disulfonic acid, and 1-naphthol-6-(4-amino-3-sulfo)anilino-3-sulfonic acid.

Preferred examples of these anions are, for example, chlorine ion, bromine ion; perchlorate ion, iodine ion, tetrafluoroborate ion, hexafluorophosphonate ion, hexafluoroantimonate ion, trifluoromethanesulfonate ion and toluenesulfonate ion.

iv) Compounds of Formula (5)

As the alkyl group, those having 1 to 10, especially 1 to 6 carbon atoms, such as methyl, ethyl, propyl and butyl, are preferred. As the aryl group, phenyl and naphthyl groups can be cited. As the alkylthio group, those having 1 to 10, especially 1 to 6 carbon atoms, such as methylthio, ethylthio, propylthio and butylthio are preferred. As the arylthio group, phenylthio and naphthylthio groups can be cited.

These alkyl, aryl, alkylthio and arylthio groups may have a substituent(s). Examples of such substituents are halogen atom (fluorine atom, chlorine atom, bromine atom, etc.), C1–C6 alkylamino or dialkylamino group, C1–C6 alkoxyl group, C1–C6 acyl group, and C1–C6 alkyl group. The number of the substituents allowed to exist is preferably 1 to 5.

When $R_1$ and $R_2$, and/or $R_3$ and $R_4$ are combined to form a ring, such a ring is, for instance, a C5–C7 aromatic ring or heterocyclic ring. The said substituent(s) may be present in this ring.

M may be charged, and the compounds of the formula (5) may take a salt structure with cations.

v) Compounds of Formula (6)

As the typical examples of the rings A, B and C, the nitrogen-containing condensed rings of the following formulae can be cited:

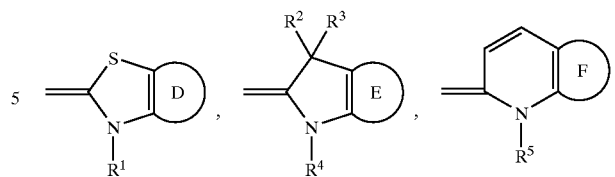

Rings A, B and C in the above formulae may be identical or different. Rings D, E and F may be independently of each other a benzene ring or a naphthalin ring which may have a substituent(s). Preferred examples of such substituents are lower alkyl groups such as methyl and ethyl group, lower alkoxyl groups such as methoxy and ethoxy group, halogen atoms such as chlorine atom and bromine atom, halogen-substituted alkyl groups, for instance, perfluoroalkyl groups such as trifluoromethyl and pentafluoroethyl, sulfonic acid group, carboxylic acid group, hydroxyl group, and phosphoric acid group. These sibstituents, two or more of them, may be bonding.

$R^1$, $R^4$ and $R^5$ may be, for instance, alkyl groups which may have a substituent(s). Such alkyl groups include C1–C8 non-substituted alkyl groups such as methyl, ethyl, n-propyl, n-butyl, n-hexyl and n-octyl group; alkyl groups having 1 to 4 ether groups such as methoxyethyl, ethoxyethyl, methoxypropyl and methoxyethoxyethoxyethyl group; alkyl groups substituted with an aryl group, for example, optionally substituted phenyl groups, such as phenylethyl and phenylpropyl group; alkyl groups substituted with an aryloxy group, for example, optionally substituted phenoxy groups, such as phenoxyethyl and phenoxypropyl group; alkyl groups substituted with a halogen atom such as fluorine atom, chlorine atom or bromine atom; and other alkyl groups having as substituent an ester group, cyano group, nitro group, thioether group, carbonyl group, sulfonyl group, amino group, substituted amino group, amide group, thioamide group, hydroxyl group, thiol group, carboxylic acid ester group, sulfonic group, furyl group;, tetrahydrofuryl group or the like.

$R^2$ and $R^3$ represent respectively an alkyl group. They may be linked to each other to form a ring. Examples of the alkyl groups represented by these R's are lower alkyl groups such as methyl, ethyl, propyl and butyl group. The ring formed by these R's may be, for instance, an aliphatic hydrocarbon ring such as a ring of cyclopentane, cyclohexane and cycloheptane, or a hydrocarbon ring which may have a crosslinking structure such a ring of norbornane, adamantane and bicyclo[3.3.1]nonane.

Examples of the benzene rings substituted with an alkylamino group of X include those represented by the formula:

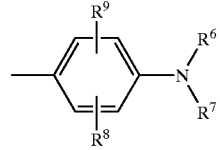

$R^6$ and $R^7$ may be the same alkyl groups as designated by $R^1$, $R^4$ and $R^5$. The alkyl groups of $R^6$ and $R^7$ may be combined with a phenyl group to form a nitrogen-containing 5-, 6- or 7-member ring, or may further form a condensed ring with a phenyl group.

$R^8$ and $R^9$ represent respectively a hydrogen atom, an optionally substituted alkyl group, an optionally substituted alkoxyl group, an acylamino group. The optionally substituted alkyl groups represented by $R^8$ and $R^9$ include nonsubstituted C1–C8 alkyl groups such as methyl, ethyl, n-propyl, n-butyl, n-hexyl and n-octyl group; and alkyl groups having 1 to 4 ether groups such as methoxyethyl, ethoxyethyl, ethoxypropyl and methoxyethoxyethoxyethyl group. The optionally substituted alkoxyl groups include nonsubstituted C1–C8 alkoxyl groups such as methoxy, ethoxy, n-propyloxy, n-butyloxy, n-hexylocy and n-octyloxy group; alkoxyl groups having 1 to 4 ether groups such as methoxyethoxy, ethoxyethoxy, methoxypropyloxy and methoxyethoxyethoxy group. The acylamino groups include alkylcarbonylamino groups such as acetylamino and propionylamino group.

vi) Compounds of Formula (7)

M represents a chelatable metal ion, which shows such as nickel ion, copper ion, cobalt ion, iron ion and zinc ion. Nickel ion and copper ion are preferred.

The substituents of alkyl, aryl, arylalkyl, alkoxyl, alkylamino and alkylaminocarbonyl groups represented by $R_1$ include, for example, halogen atoms (fluorine atom, chlorine atom, etc.), alkyl groups, aryl groups, heterocyclic groups, nitro groups, cyano groups, alkoxyl groups, aryloxy groups, alkylthio groups, arylthio groups, keto groups, sulfonamide groups, sulfamoyl groups, acylamino groups, carbamoyl groups, sulfonyl groups, sulfinyl groups, hydroxyl groups, carboxyl groups, amino groups, and primary and secondary amino groups.

As the alkyl groups, they include straight-chain or branched alkyl groups having preferably 1 to 8, more preferably 1 to 6 carbon atoms, such as methyl, ethyl, propyl, butyl and octyl. The aryl groups are preferably phenyl groups.

As the alkoxyl groups, they include methoxy, ethoxy, n-propoxy, iso-propoxy, n-butoxy and iso-butoxy groups. As the alkylaminocarbonyl groups, they include N-methylaminocarbonyl, N-ethylaminocarbonyl, N-n-propylaminocarbonyl, N-iso-propylaminocarbonyl, N-n-butylaminocarbonyl, N-iso-butylaminocarbonyl, N,N-dimethylaminocarbonyl, N,N-diethylaminocarbonyl, N,N-n-dipropylaminocarbonyl, N,N-iso-dipropylaminocarbonyl, N,N-n-dibutylaminocarbonyl and N,N-isodibutylaminocarbonyl groups. As the acylamino groups, they include acetylamino, propionylamino and benzoylamino groups.

$R^2$ and $R^3$ represent a halogen atom or a monovalent organic group. The halogen atom is preferably chlorine atom or fluorine atom. The monovalent organic group is preferably selected from the optionally substituted alkyl groups (C1–C8 alkyl groups such as methyl and ethyl group), the optionally substituted alkoxyl groups (C1–C10 alkoxyl groups such as methoxy and ethoxy), —$CONR^7R^8$, —$NHCOR^9$, —$NHCO_2R^9$, —$NHSO_2R^9$, —$NHSO_2NR^7R^8$, —$COOR^9$, —$SO_2R^9$, —$NHCONR^7R^8$ and cyano groups. In the above formulae, $R^7$ and $R^8$ represent individually a hydrogen atom, an alkyl group having preferably 1 to 8 carbon atoms, a cycloalkyl group, an aryl group such as phenyl group, or a heterocyclic group such as pyridyl and furyl group. $R^9$ represents a hydrogen atom, an alkyl group having preferably 1 to 8 carbon atoms, an aryl group such as phenyl group, a cycloalkyl group, a heterocyclic group such as pyridyl and furyl group, or an amino group. Each group may have a substituent.

Examples of such substituents are halogen atoms (fluorine atom, chlorine atom, etc.), C1–C6 alkyl groups, aryl groups such as phenyl group, heterocyclic groups such as pyridyl and furyl group, nitro groups, cyano groups, C1–C4 alkoxyl groups, aryloxy groups such as phenyloxy group, C1–C4 alkylthio groups, arylthio groups such as phenylthio group, keto groups, sulfonamide groups, sulfamoyl groups, C1–C4 acylamino groups, carbamoyl groups, sulfonyl groups, sulfinyl groups, hydroxyl groups, carboxyl groups, amino groups, and primary and secondary C1–C4 amino groups.

It is especially preferable that the alkyl groups represented by $R^4$, $R^5$ and $R^6$ are C1–C4 alkyl groups (such as methyl, ethyl, n-propyl or n-butyl group). These alkyl groups include those having a substituent(s). Preferred examples of such substituents are hydroxyl groups, alkoxyl groups (such as methoxy or ethoxy group), alkylsulfonamide groups (such as methanefulonamide group), sulfo groups, carboxyl groups, sulfamoyl groups and carbamoyl groups.

The anions represented by $Z^-$ are those commonly known in the art, preferably, for instance, $I^-$, $Br^-$, $Cl^-$, $ClO^{4-}$, $CH_3COO^-$, $BF_3^-$

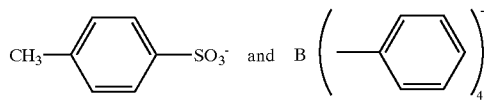

vii) Compounds of Formulae (8) to (11)

$X^e$ represents an anion such as chlorine ion, bromine ion, iodine ion, perchlorate ion, benzenesulfonate ion, p-toluenesulfonate ion, methyl sulfate ion, ethylsulfate ion, propylsulfate ion, tetrafluoroborate ion, tetraphenyl borate ion, hexafluorophosphate ion, benzenesulfinate ion, acetate ion, trifluoroacetate ion, propionate ion, benzoate ion, oxalate ion, succinate ion, malonate ion, oleate ion, stearate ion, citrate ion, hydrogenphosphate ion, dihydrogenphosphate ion, pentachlorostannate ion, chlorosulfonate ion, fluorosulfonate ion, trifluoromethanesulfonate ion, hexafluoroantimonate ion, hexafluoroarsenate ion, molybdenate ion, tungstate ion, titanate ion, and zirconate ion.

The following can be named as examples of $R^1$ to $R^7$: hydrogen atoms, deuterium, halogen atoms (F, Cl, Br and I atom), alkyl groups (C1–C12 alkyl groups such as methyl, ethyl, n-propyl, iso-propyl, n-butyl, sec-butyl, iso-butyl, t-butyl, n-amyl, t-amyl, n-hexyl, n-octyl, t-octyl and dodecyl group), other alkyl groups, for example, substituted alkyl groups (C1–C12 alkyl groups substituted with a halogen atom, an alkoxyl group, etc., such as 2-hydroxyethyl, 3-hydroxypropyl, 4-hydroxybutyl, 2-methoxyethyl, 2-ethoxyethyl, 3-methoxypropyl, 3-ethoxypropyl, 2-chloroethyl, 3-chloropropyl, 2-fluoroethyl, 3-fluoroethyl, trifluoromethyl, pentafluoroethyl, 2,2,2-trifluoroethyl, 2-acetoxyethyl, carboxymethyl, 2-carboxyethyl, 3-carboxypropyl, 2-sulfoethyl, 3-sulfopropyl, 4-sulfobutyl, 3-sulfatepropyl, 4-sulfatebutyl, N-(methylsulfonyl)-carbamylmethyl, 3-(acetylsulfamyl)propyl, 4-(acetylsulfamyl)butyl, 2-methoxycarbonylethyl, 2-ethoxycarbonylethyl, 3-methoxycarbonylpropyl, 3-ethoxycarbonylpropyl, 2-benzyloxyethyl, 3-benzyloxypropyl, 2-aminoethyl, 2-dimethylaminoethyl, 2-nitroethyl and 2-cyanoethyl group), cyclic alkyl groups (C1–C12 cyclic alkyl groups such as cyclopropyl, cyclopentyl, cyclohexyl and cycloheptyl group), allyl groups (e.g., C1–C12 allyl groups such as allyl, isobutenyl and prenyl group), alkenyl groups (C1–C12 alkenyl groups such as vinyl, propenyl, isopropenyl, butenyl, pentenyl, hexenyl, octenyl or dodecenyl group), aralkyl groups (C1–C12 aralkyl groups such as benzyl, 2-phenylethyl, 3-phenylpropyl, α-naphthylmethyl and β-naphthylmethyl group), substituted aralkyl groups (such as carboxybenzyl, sulfobenzyl, hydroxybenzyl, methoxybenzyl, ethoxybenzyl, nitrobenzyl, xylylenyl, aminobenzyl, methoxycarbonylbenzyl, chlorobenzyl or fluorobenzyl group), acyl groups (C1–C12 acyl groups such as acetyl, propionyl, butyroyl, valeroyl, benzoyl, tolyoyl, naphthoyl and phthaloyl group), amino groups (such as amino, dimethylamino, diethylamino, dipropylamino; dibutylamino, acetylamino, benzoylamino, diphenylamino, di-p-dimethylaminophenylamino and di-p-diethylaminophenylamino group), thiol groups, substituted thio groups (such as methylthio, ethylthio, propylthio, butylthio, benzylthio, phenylthio, 2,4-dinitrophenylthio, p-methoxyphenylthio, p-aminophenylthio and p-dimethylaminophenylthio group), substituted or non-substituted aryl groups (such as phenyl, naphthyl, tolyl, xylyl, anthranyl, pyrenyl, fluorophenyl, chlorophenyl, ethylphenyl, hydroxyphenyl, methoxyphenyl, ethoxyphenyl, nitrophenyl, aminophenyl, dimethylaminophenyl, diethylaminophenyl, dipropylaminophenyl, dibutylaminophenyl, cyanophenyl, methylthiophenyl, phenoxyphenyl, phenylthiophenyl, 2,4-dinitrophenyl, dimethoxydiphenyl and trimethoxyphenyl group), substituted or non-substituted heterocyclic groups (such as piperidino, morphorino, pyridyl, quinolyl, lepidyl, methylpyridyl, furyl, thienyl, benzofuranyl, thionaphthyl, phenothiazyl, phenoxazyl, indolyl, pyrrolyl, carbazolyl and N-ethylcarbazolyl group), substituted or non-substituted styryl groups (such as styryl, methoxystyryl, dimethoxystyryl, trimethoxystyryl, ethoxystyryl, dimethylaminostyryl, diethylaminostyryl, dipropylaminostyryl, dibenzylaminostyryl, diphenylaminostyryl, 2,2-diphenylvinyl, 2-phenyl-2-methylvinyl, 2-(dimethylaminophenyl)-2-phenylvinyl, 2-(diethylaminophenyl)-2-phenylvinyl, 2-(dibenzylaminophenyl)-2-phenylvinyl, 2,2-di(diethylaminophenyl)vinyl, 2,2-di(methoxyphenyl)vinyl, 2,2-di(ethoxyphenyl)vinyl, 2-(dimethylaminophenyl)-2-methylvinyl and 2-(diethylaminophenyl)-2-ethylvinyl group), and substituted or non-substituted arylazo groups (such as phenylazo, α-naphthylazo, β-naphthylazo, dimethylaminophenylazo, chlorophenylazo, nitrophenylazo, methoxyphenylazo and tolylazo group).

The compounds represented by the formula (1) can be synthesized according, for example, to the synthesis process described in JP-A-63-95269. The compounds represented by the formula (2) can be synthesized according, for example, to the synthesis process described in JP-A-3-316161. The compounds represented by the formulae (3) and (4) can be synthesized according, for instance, to the synthesis process described in JP-B-43-25335. The compounds represented by the formula (5) can be synthesized by following, for example, the synthesis process described in JP-A-60-51166. The compounds represented by the formula (6) can be synthesized according, for instance, to the synthesis process described in JP-A-8-245895. The compounds represented by the formula (7) can be synthesized according, for instance, to the synthesis process described in JP-A-4-78579. The compounds represented by the formulae (8), (9), (10) and (11) can be synthesized according, for example, to the synthesis processes described in JP-A-62-123252, JP-A-3-226736, JP-A-5-313305, JP-A-6-43583, European Patent 0430244A, and J. Am. Chem. Soc., 80, 3772–3777 (1958).

The compounds of the formulae (1) to (11) may be offered in the form of their pharmacologically acceptable salts. Such salts include, besides those mentioned above, the ones which are commonly used as pharmacologically acceptable salts, for example, the salts with acids such as hydrochloride, sulfate, phosphate, citrate and p-toluenesulfonate, and the salts with bases, for example, alkali metal salts such as sodium and potassium salt, alkaline earth metal salts such as calcium salt, and organic salts such as methylamine and ethylenediamine salt.

Some representative examples of the compounds utilizable as the photochemotherapeutic agent according to the present invention are shown below. The wavelengths at which these compounds show maximum absorption (maximum absorption wavelengths) are shown in Table 1.

Representative Compounds

Polymethine type 1

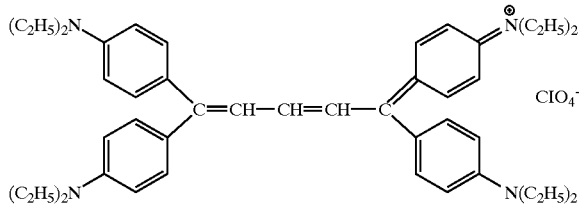

Polymethine type 2

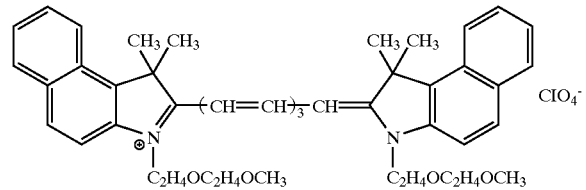

Polymethine type 3

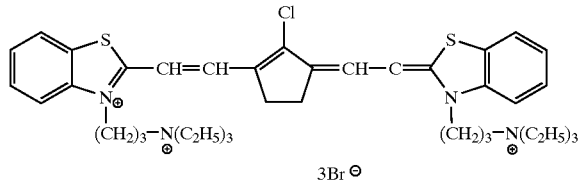

Polymethine type 4

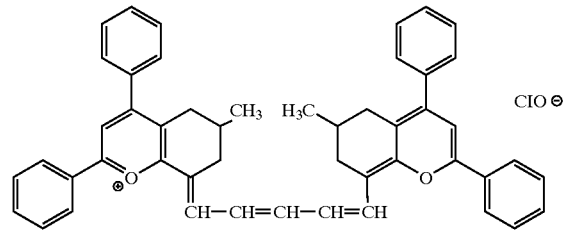

-continued
Naphthalocyanine type 5
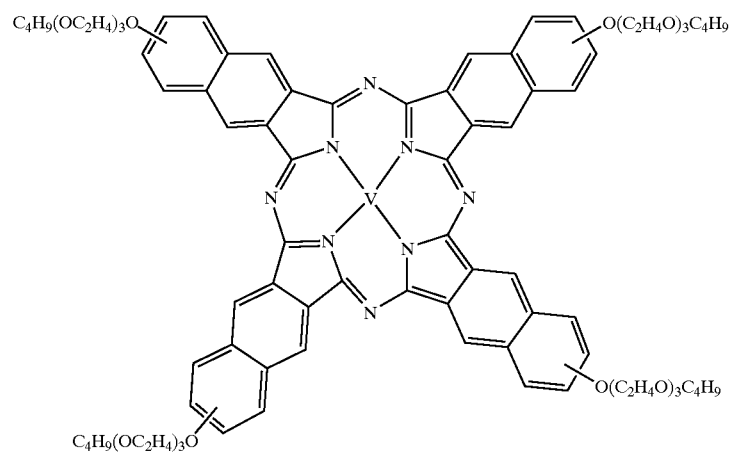
Anthracyanine type 6
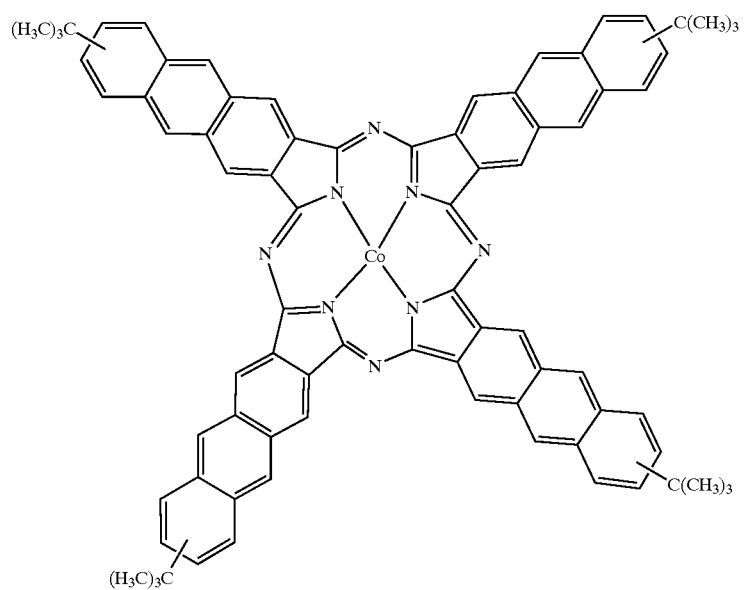
Complex type 7
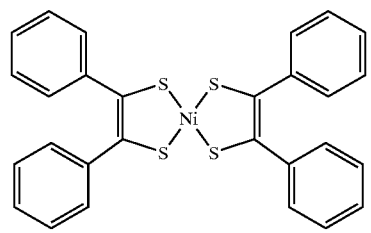
Metal-containing indoaniline type 8
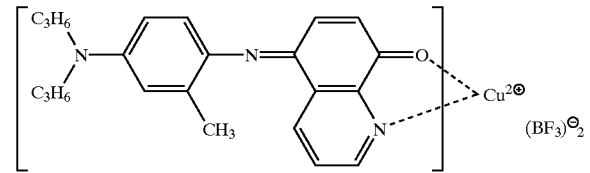

Diimonium type 9

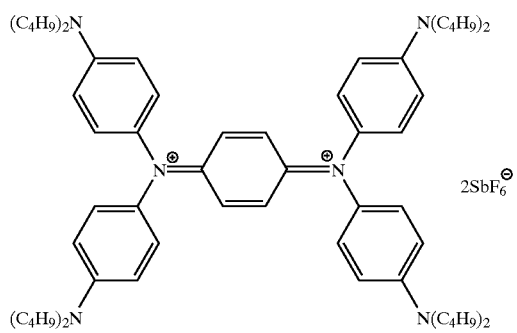

Aminium type 10

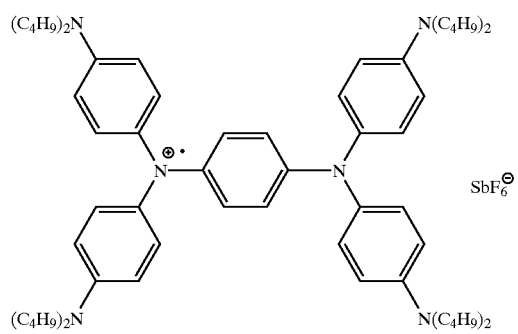

TABLE 1

Maximum absorption wavelength of the representative compounds

| Compound No. | Maximum absorption wavelength (λmax) |
| --- | --- |
| Polymethine type 1 | 820 nm |
| Polymethine type 2 | 830 |
| Polymethine type 3 | 822 |
| Polymethine type 4 | 1045 |
| Naphthalocyanine type 5 | 840 |
| Anthracyanine type 6 | 800 |
| Complex type 7 | 860 |
| Metal-containing indoaniline type 8 | 840 |
| Diimonium type 9 | 1090 |
| Aminium type 10 | 950 |

As is apparent from Table 1, all of these compounds show maximum absorption in the wavelength region of 800 to 1,200 nm and enable photochemotherapy with high absorption efficiency.

The compounds used in the present invention, especially those of the formulae (1) to (11) or their pharmacologically acceptable salts showing maximum absorption in the wavelength region of 800 to 1,200 nm, have the following characteristic features (a) Since their maximum absorption wavelength is between 800 and 1,200 nm, the compounds can be applied to the treatment down to a greater depth of living tissue.
(b) They become very active on exposure to light and can obliterate, for example, solid cancer.
(c) They have affinity for the target cell, for instance, cancerous cell, so that they are capable of very efficient treatment of the affected region.
(d) They are almost inactive to the living body not exposed to light, so that their side effects are limited.
(e) They are soluble in solvents, so that they lend themselves to preparation of various dosage forms such as injections.

The mechanism of action of the photochemotherapeutic agent of the present invention has not yet clarified sufficiently, but it is considered that the therapeutical effect of the agent can be attributed to the heat-up effect of the compounds produced by their exothermal action and to the generation of free radicals or analogous molecular species in the molecule. Especially in the case of aminium type compounds, since they have free radicals in the molecule, the action by these free radicals is considered also.

The photochemotherapeutic agent of the present invention exhibits a therapeutic effect against thrombosis, arteriosclerosis, diseases of the cardiovascular system, etc., but it is useful as a therapeutic agent for tumors, especially carcinomas, and can be used for therapy of cancers which grow in the deep region of the body.

The photochemotherapeutic agent of present invention is provided in the form of commonly used medicinal and pharmaceutical preparations such as injection, tablet, powder, etc. In producing such preparations, it is possible to use the ordinarily employed pharmacologically acceptable carriers such as, for example, binder, lubricant, disintegrator, solvent, excipient, solubilizer, dispersant, stabilizer, suspending agent, preservative, anodyne, colorant, spicery, etc. In the case of injections, usually a solvent is used. As the solvent, there can be used, for instance, physiological saline, 5% glucose or mannitol solution, water-soluble organic solvents such as glycerol, ethanol, dimethyl sulfoxide and polyethylene glycol, Cremophor, and mixtures of such water-soluble organic solvents with water. The amount of the compound showing maximum absorption in the wavelength region of 800 to 1,200 nm in the preparations, although variable depending on the type of the compound used and dosage form, is ordinarily 0.1 to 100% by weight. In the case of injections, a compound showing maximum absorption in the wavelength region of 800 to 1,200 nm is preferably contained to a concentration of 0.1 to 100 mg/ml. The solvent to be used varies depending on the type of the compound used. It is possible to use, for instance, water (physiological saline, etc.) or water-soluble organic solvents (ethanol, dimethyl sulfoxide; etc.). Also, the solvents may be used either singly or as a mixture of two or more of them.

Dose of the photochemotherapeutic agent of the present invention varies according to the patient's age, patient's body weight, condition of the disease, therapeutical effect, route of administration, time and period (days) of administration, and other factors, but usually the agent is administered once every two to four weeks, 3 to 6 times in all, at a dose of 10 to 500 mg, preferably once every four weeks, 5 times in all, at a dose of 100 to 500 mg.

The method for photochemotherapy of tumors according to the present invention characterized in administering the said photochemotherapeutic agent and then applying light rays of a wavelength region of 800 to 1,200 nm. As the tumors, that can be treated is solid tumors, which can be classified into benign tumors and malignant tumors. Benign tumors include, for instance, papilloma, adenoma (polyp), lipoma, hemangioma, lymphangioma, fibroma and lentigo, and malignant tumors include carcinosis and sarcoma. Administration can be effected either orally or parenterally, although parenteral administration is recommendable. Injection can be performed intravenously, intraarterially, subcutaneously or directly to the affected region (site of tumor). Preferably, the agent is made into a liniment such as salve and applied to the surface of the tumor, or the agent is formed into an injection and injected directly into the tumor.

Light used for the photochemotherapy of the present invention, may be of any type as far as it is of a wavelength substantially equal to the maximum absorption wavelength of the compound contained in the agent or of a wavelength band embracing the maximum absorption wavelength of the compound. Usually light rays of a wavelength region of 800 to 1,200 nm, preferably laser light of that wavelength, are used. The exposure dose of light varies depending on the type and condition of the therapeutic target, the condition, age, sex, body weight and constitution of the patient, the type of the compound used, etc., but it is usually in the range of 10 to 200 J/cm$^2$. It is possible to use either only one type of light of a single wavelength or a single band of wavelength or to use two or more types of light of different wavelengths or different bands of wavelength.

The present invention will be described in further detail by showing the examples thereof, but the scope of the present invention is not restricted by these examples.

EXAMPLE 1

Acute Toxicity Test on Mice

1) Method

A diimonium type compound 9 or an aminium type compound 10 was dissolved in dimethyl sulfoxide and the concentration of each solution was adjusted so that the compound would be given at a dose of 150 mg/kg, 100 mg/kg, 25 mg/kg or 6.25 mg/kg. Each solution was administered once intraperitoneally to the CDF1 (female) mice in an amount of 0.05 ml per 20 g of mouse body weight.

2) Result

Administration of the diimonium type compound 9 or the aminium type compound 10 caused no death of mouse even at the setting dose of 150 mg/kg. Also, after administration, there took place no decrease of body weight, nor was observed any indication of toxicity of either compound.

EXAMPLE 2

Antitumor Effect on Human Pharynx Cancer HEp-2

1) Method

Human pharynx cancer HEp-2 specimen was sliced into a 2 mm$^3$ cube, and it was transplanted under the skin of a back side region of a BALB/c (female) nude mouse by a trocar. When this tumor grew up to a volume of about 200 mm$^3$, it was used for the therapeutic experiment. A dimethyl sulfoxide solution of the diimonium type compound 9 or the aminium type compound 10 was prepared with its concentration adjusted so that the dose of the compound would become 150 mg/kg. 50 $\mu$l of this solution was administered to the region of tumor of the mouse under anesthesia, and immediately thereafter, semiconductor laser light of a wavelength of 980 nm was applied to the region for 10 minutes at an irradiation dose of 500 mW/cm$^2$ to conduct the photodynamic therapy for cancer. The mouse which had laser irradiation alone, was compared as control.

2) Result

In the mouse subjected to the photodynamic therapy using the said diimonium type compound 9 or the aminium type compound 10, the tumor region was blackened and formed the crust the day after laser irradiation. 15 days after irradiation, the crust fell off and the tumor completely disappeared. In the mouse (control) which had laser irradiation alone, on the other hand, merely slight white spots were formed at the region of tumor and the tumor kept on growing.

EXAMPLE 3

Antitumor Effect of 1064 nm Laser Irradiation on Human Pharynx Cancer HEp-2

1) Method

Human pharynx cancer HEp-2 was transplanted to the nude mouse in the same way as in Example 2, and when the volume of the tumor became 100 mm$^3$ or greater, it was used for the therapeutic experiment. 50 $\mu$l of a dimethyl sulfoxide solution of the diimonium type compound 9 or the aminium type compound 10, with its concentration adjusted so that the compound would be given at a dose of 37.5 mg/kg or 150 mg/kg, was administered to the region of tumor, and immediately thereafter, Nd-YAG laser with a wavelength of 1,064 nm was applied to the region of tumor at an irradiation dose of 300 J/cm$^2$ to conduct the photodynamic therapy. The mouse, which had laser irradiation alone, was compared as control.

2) Result

In the mouse subjected to the photodynamic therapy using the diimonium type compound 9 or the aminium type compound 10, the region of tumor was blackened and formed the crust the day after laser irradiation, and eventually the tumor was necrotized. Remarkably, in the case using the diimonium type compound 9, the tumor was entirely incrusted and its growth was strongly suppressed. However, in the case of the control mouse which had laser irradiation alone and in the case where the diimonium type compound 9 or the aminium type compound 10 was administered but no laser irradiation was conducted, necrotization of the tumor did not occur. Results are shown in Table 2.

TABLE 2

| Tumor-necrotizing action of the compounds of the present invention | | | |
|---|---|---|---|
| Compounds of this invention | Dose of compound (mg/kg) | Irradiation dose (J/cm$^2$) | Effect |
| Control | | 300 | Tumor grew. |
| Diimonium type compound 9 | 37.5 | 0 | Tumor grew. |
| | | 300 | Tumor necrotized. |
| Aminium type compound 4 | 150 | 0 | Tumor grew. |
| | | 300 | Tumor necrotized in part |

EXAMPLE 4

Blood Flow Stasis Effect

1) Method

Blood flow in the subcutaneous blood vessel of the nude mouse or in the blood vessel induced by the tumor transplanted in the same way as in Example 2 was observed under a microscope. The diimonium type compound 9 or the aminium type compound 10 was administered subcutaneously, or directly into the tumor, and several minutes thereafter, semiconductor laser light of 980 nm was applied to the compound-administered region at an irradiation dose of 165 or 250 J/cm$^2$. The image of blood flow at the irradiated region was monitored continuously by a CCD camera and videorecorded.

2) Result

Blood flow in the blood vessel at the diimonium type compound 9 or the aminium type compound 10 administered region and its vicinity was intercepted by the application of laser light. Results are shown in Table 3.

TABLE 3

Blood flow stasis effect of the compounds of the present invention

| Compound of this invention | Concentration (mg/ml) | Administered region | Irradiation dose (J/cm$^2$) | Blood flow stasis effect |
|---|---|---|---|---|
| Control | | | 250 | None |
| Diimonium type compound 9 | 5 | Subcutaneous | 250 | Partial |
| | | Into tumor | 250 | Partial |
| | 50 | Subcutaneous | 250 | Strong |
| Aminium type compound 10 | 5 | Subcutaneous | 250 | Partial |

Notes:
Strong: Almost whole of the blood flow at the compound-administered region and its vicinity is perfectly intercepted.
Partial: Part of the blood flow at the compound-administered region and its vicinity is perfectly intercepted.
Weak: Blood flow at the compound-administered region and its vicinity is imperfectly intercepted.
None: Blood flow at the compound-administered region and its vicinity is not intercepted.

It is suggested that the diimonium type compound 9 or the aminium type compound 10 is reacted with laser light to generate free radicals, and these free radicals give an injurious effect to the endothelium of the blood vessel to cause thrombosis.

Industrial Applicability

A photochemotherapeutic agent for tumors, especially for carcinomas, is realized by use of the therapeutic agent of the present invention which is of the utterly different type from the conventional porphyrin-based drugs. Also, the active ingredient of the therapeutic agent of the present invention shows maximum absorption in the long wavelength region of 800 to 1,200 nm and has strong absorbance, so that it enables highly efficient treatment of tumors. Further, since this range of wavelength shows high tissue penetrability, therapy of tumors which grow in the deep region of the body, especially carcinomas, is made possible.

What is claimed is:

1. A photochemotherapeutic composition comprising a diimonium compound represent by the following formula (3) or its pharmacologically acceptable salts, and a pharmacologically acceptable carrier:

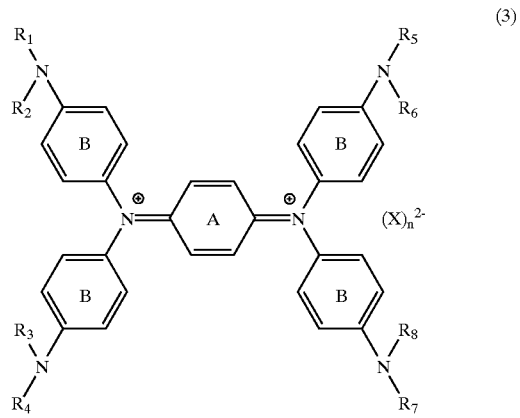

wherein $R_1$ to $R_8$ represent independently a C1–C12 substituent selected from the group consisting of alkyl group, alkoxyalkyl group, alkenyl group, aralkyl group and alkynyl group, X represents an anion, n is a number of 1 or 2, and ring A and four ring B's may have independently of each other 1to 4 substituents.

2. A photochemotherapeutic composition according to claim 1, wherein $R_1$ to $R_8$ are each a C1–C5 alkyl group, and ring A and four ring B's have no substituent.

3. A photochemotherapeutic composition according to claim 1, wherein the pharmacologically acceptable carrier is a solvent.

4. A photochemotherapeutic composition according to claim 3, containing a compound represented by the formula (3) or its pharmacologically acceptable salt in a concentration of 0.1 to 100 mg/ml.

5. A photochemotherapeutic composition according to claim 3, wherein the solvent is a physiological saline solution, a 5% glucose solution or a mannitol solution.

6. A photochemotherapeutic composition according to claim 3, wherein the solvent is a water-soluble organic solvent selected from the group consisting of glycerol, ethanol, dimethyl sulfoxide, polyethylene glycol and Cremophor.

7. A photochemotherapeutic composition according to claim 3, wherein the solvent is a mixture of water and a water-soluble organic solvent.

8. A photochemotherapeutic composition according to claim 6, wherein the water-soluble organic solvent is dimethyl sulfoxide or ethanol.

* * * * *